(12) United States Patent
Vogt et al.

(10) Patent No.: US 11,103,295 B2
(45) Date of Patent: Aug. 31, 2021

(54) BONE CEMENT APPLICATION DEVICE WITH CLOSURE ON THE DELIVERY PLUNGER

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

(*) Notice: Subject to any disclaimer, the term of this patent is extended or adjusted under 35 U.S.C. 154(b) by 272 days.

(21) Appl. No.: 15/964,676

(22) Filed: Apr. 27, 2018

(65) Prior Publication Data

US 2018/0310974 A1    Nov. 1, 2018

(30) Foreign Application Priority Data

Apr. 28, 2017    (DE) ..................... 10 2017 109 255.2

(51) Int. Cl.
*B01F 15/02* (2006.01)
*A61B 17/88* (2006.01)
(Continued)

(52) U.S. Cl.
CPC ...... *A61B 17/8825* (2013.01); *A61B 17/8827* (2013.01); *B01F 3/12* (2013.01);
(Continued)

(58) Field of Classification Search
CPC ................................................ B01F 15/0237
(Continued)

(56) References Cited

U.S. PATENT DOCUMENTS

| 71,696 A | * | 12/1867 | Carver ................. | B01F 13/002 |
| | | | | 366/130 |
| 2,446,501 A | | 8/1948 | Weber | |

(Continued)

FOREIGN PATENT DOCUMENTS

| DE | 2060626 | 6/1972 |
| DE | 3640279 | 6/1987 |

(Continued)

OTHER PUBLICATIONS

Charnley, J., "Anchorage of the Femoral Head Prosthesis of the Shaft of the Femur," The Journal of Bone and Joint Surgery, 42 B, No. 1, pp. 28-30 (Feb. 1960).

(Continued)

*Primary Examiner* — David L Sorkin
(74) *Attorney, Agent, or Firm* — Dicke, Billig & Czaja, PLLC

(57) ABSTRACT

One aspect relates to a device for producing a bone cement paste from a monomer liquid and a cement powder as parent components of the bone cement paste and for delivering the mixed bone cement paste, the device having a cartridge having a cylindrical interior. The interior of the cartridge is closed on the front side except for a delivery opening for expelling the bone cement paste. A delivery plunger is arranged in the interior of the cartridge. The cement powder is arranged in the interior of the cartridge. A closure is arranged on the front side of the delivery plunger. The closure closes the delivery opening when the delivery plunger is pressed against the front side of the interior of the cartridge. The closure blocks a further movement of the delivery plunger so that the delivery plunger is spaced from the front side of the interior of the cartridge at least in some areas and a dead volume remains in the interior of the (Continued)

cartridge when the delivery plunger is pressed against the front side of the interior of the cartridge.

38 Claims, 9 Drawing Sheets

(51) Int. Cl.
 *B01F 3/12* (2006.01)
 *B01F 13/00* (2006.01)

(52) U.S. Cl.
 CPC ...... *B01F 13/0023* (2013.01); *B01F 13/0027* (2013.01); *B01F 15/0206* (2013.01); *B01F 15/0223* (2013.01); *B01F 15/0225* (2013.01); *B01F 15/0237* (2013.01); *B01F 15/0279* (2013.01); *A61B 17/8816* (2013.01); *A61B 2017/8838* (2013.01); *B01F 2003/1257* (2013.01); *B01F 2215/0029* (2013.01)

(58) Field of Classification Search
 USPC ................................ 366/130, 189; 604/87
 See application file for complete search history.

(56) References Cited

U.S. PATENT DOCUMENTS

| | | | |
|---|---|---|---|
| 2,869,543 A * | 1/1959 | Ratcliff | A61M 5/19 604/90 |
| 3,785,379 A | 1/1974 | Cohen | |
| 4,116,240 A * | 9/1978 | Guiney | A61M 5/31596 604/191 |
| 4,671,263 A | 6/1987 | Draenert | |
| 4,676,406 A | 6/1987 | Frischmann et al. | |
| 4,737,036 A * | 4/1988 | Offermann | A23G 3/0221 366/130 |
| 4,758,096 A | 7/1988 | Gunnarsson | |
| 4,973,168 A | 11/1990 | Chan | |
| 5,100,241 A | 3/1992 | Chan | |
| 5,344,232 A | 9/1994 | Nelson et al. | |
| 5,476,449 A * | 12/1995 | Richmond | A61M 5/31596 604/191 |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,033,105 A | 3/2000 | Barker et al. | |
| 6,367,962 B1 | 4/2002 | Mizutani et al. | |
| 6,709,149 B1 | 3/2004 | Tepic | |
| 6,935,541 B1 | 8/2005 | Campbell et al. | |
| 7,018,089 B2 | 3/2006 | Wenz et al. | |
| 2004/0074927 A1 | 4/2004 | Lafond | |
| 2008/0312588 A1 | 12/2008 | Faccioli et al. | |
| 2011/0308665 A1 | 12/2011 | McKay | |
| 2014/0198601 A1 | 7/2014 | Lidgren et al. | |
| 2014/0269147 A1 | 9/2014 | Click et al. | |

FOREIGN PATENT DOCUMENTS

| | | |
|---|---|---|
| DE | 69812726 | 2/2004 |
| DE | 202005010206 | 10/2005 |
| DE | 102009031178 | 9/2010 |
| EP | 0692229 | 1/1996 |
| EP | 0796653 | 9/1997 |
| EP | 1005901 | 6/2000 |
| EP | 1016452 | 7/2000 |
| EP | 1020167 | 7/2000 |
| EP | 1219262 | 7/2002 |
| EP | 1886647 | 2/2008 |
| WO | 9426403 | 11/1994 |
| WO | 9967015 | 12/1999 |
| WO | 0035506 | 6/2000 |
| WO | 2011089480 | 7/2011 |
| WO | 2012115022 | 8/2012 |

OTHER PUBLICATIONS

Kühn, Klaus-Dieter, "Bone Cements," Springer-Verlag, pp. 9 (2000).

* cited by examiner

BONE CEMENT APPLICATION DEVICE WITH CLOSURE ON THE DELIVERY PLUNGER

CROSS-REFERENCE TO RELATED APPLICATION

This Utility Patent Application claims priority to European Patent Application No. DE 10 2017 109 255.2, filed on Apr. 28, 2017, which is incorporated herein by reference.

BACKGROUND

One aspect relates to a device for producing a bone cement paste from a monomer liquid and a cement powder as parent components of the bone cement paste and for delivering the mixed bone cement paste. One aspect also relates to a method for producing a bone cement paste, in particular a paste-like polymethyl methacrylate bone cement paste, with such a device.

The subject matter of the device is, for example, a device for separately storing the cement powder and the monomer liquid of polymethyl methacrylate bone cement, for subsequently mixing the cement powder with the monomer liquid to form a bone cement paste, and for delivering the mixed bone cement paste. The device according a full-prepacked cementing system.

Polymethyl methacrylate (PMMA) bone cements date back to the fundamental work of Sir Charnley (Charnley, J.: Anchorage of the femoral head prosthesis of the shaft of the femur. J. Bone Joint Surg. 42 (1960) 28-30). Conventional polymethyl methacrylate bone cements (PMMA bone cements) are composed of a component in powder form and a liquid monomer component (K.-D. Kühn: Knochenzemente für die Endoprothetik: Ein aktueller Vergleich der physikalischen and chemischen Eigenschaften handelsüblicher PMMA-Zemente [Bone cements for endoprosthetics: A current comparison of the physical and chemical properties of commercial PMMA cements], Springer-Verlag Berlin Heidelberg New York, 2001). The monomer component generally contains the monomer methyl methacrylate and an activator (N,N-dimethyl-p-toluidine) dissolved therein. The powder component, also referred to as cement powder or bone cement powder, includes one or more polymers, which are produced on the basis of methyl methacrylate and comonomers, such as styrene, methyl acrylate or similar monomers through polymerization, for example, suspension polymerization, a radiopaque substance and the initiator di-benzoyl peroxide. When the powder component is mixed with the monomer component, a plastically deformable paste, the actual bone cement or bone cement paste, is produced as a result of the expansion of the polymers of the powder component in the methyl methacrylate. When the powder component is mixed with the monomer component, the activator N,N-dimethyl-p-toluidine reacts with di-benzoyl peroxide to form radicals. The radicals formed initiate the radical polymerization of the methyl methacrylate. With the continuing polymerization of the methyl methacrylate, the viscosity of the bone cement paste increases until it solidifies.

PMMA bone cements can be mixed in suitable mixing beakers with the aid of spatulas by mixing the cement powder with the monomer liquid. In this case, air bubbles can become included in the bone cement paste, which can have a negative influence on the mechanical properties of the hardened bone cement.

To prevent air inclusions in the bone cement paste, a plurality of vacuum cementing systems are described, of which the following are mentioned by way of example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

A further development in cementing technology is represented by cementing systems in which both the cement powder and the monomer liquid are already packed in separate compartments of the mixing devices and are not mixed with one another in the cementing system until immediately prior to the cement application. Such closed full-prepacked mixing devices have been proposed by EP 0 692 229 A1, DE 10 2009 031 178 B3, U.S. Pat. Nos. 5,997,544 A, 6,709,149 B1, DE 698 12 726 T2, EP 0 796 653 A2 and U.S. Pat. No. 5,588,745 A.

Patent DE 10 2009 031 178 B3 discloses a storage and mixing device as a full-prepacked mixing device, in which the parent components required for producing the bone cement paste are already stored in the storage and mixing device and can be combined and mixed in the storage and mixing device. The storage and mixing device has a two-part delivery plunger for closing a cement cartridge. In this case, a combination of a gas-permeable sterilization plunger and a gas-impermeable sealing plunger are used.

Polymethyl methacrylate bone cements are applied in the not yet hardened, paste-like state as a bone cement paste after mixing the cement powder with the liquid monomer component. When using mixing devices, the bone cement paste in the case of powder/liquid cements is located in a cartridge. During the application of such conventional PMMA bone cements, after mixing the two parent components, the bone cement paste formed is pressed out with the aid of manually operable pressing-out devices. The bone cement paste is pushed out of the cartridge by the movement of a delivery plunger. The delivery plungers conventionally have a diameter between 30 mm and 40 mm and therefore an area of 7.0 $cm^2$ to 12.5 $cm^2$ on the outer side on which a tappet or a rod of the pressing-out device acts during the pressing-out procedure.

The movement of the delivery plunger is, for example, effected by manually operable, mechanical pressing-out devices. These manual pressing-out devices normally reach a pressing-out force in the region of approximately 1.5 kN to 3.5 kN.

These simple mechanical pressing-out devices use clamping rods, which are driven by a manually actuated tilt lever, for the pressing-out procedure. The manually driven pressing-out devices have been proven worldwide for decades and hitherto represent the prior art. These pressing-out devices allow that the medical operator gains a sense of the penetration resistance of the bone cement paste into the bone structures (spongiosa) via the manual force to be applied.

When using all the hitherto-known full-prepacked mixing devices, the medical operator has to successively carry out a plurality of operating steps on the devices in a predetermined sequence until the mixed bone cement paste is present and can be applied. Mixing up the operating steps can lead to failure of the mixing device and therefore cause disruption to the surgical procedure. Cost-intensive training of the medical operator is therefore necessary to prevent operator errors.

In WO 00/35506, a device is proposed in which polymethyl methacrylate cement powder is stored in a cartridge, wherein the cement powder fills the entire volume of the cartridge and the volume of the clearances between the particles of the cement powder is such that it corresponds to the volume of the monomer liquid required to produce the bone cement paste with the cement powder stored in the cartridge. This device is constructed such that the monomer liquid is introduced into the cartridge from above as a result of a vacuum effect, wherein, to this end, a vacuum is applied to the underside of the cartridge at a vacuum connection. The monomer liquid is thus drawn through the cement powder, wherein air located in the clearances between the cement powder particles is displaced by the monomer liquid. In this case, mechanical mixing of the formed cement paste by means of a stirrer is omitted.

This system can be disadvantageous in that cement powders which expand rapidly with the monomer liquid cannot be mixed with this device because, after the monomer liquid has penetrated approximately 1 to 2 cm into the cement powder, the rapidly expanding cement powder particles form a gel-like barrier and obstruct the migration of the monomer liquid through the entirety of the cement powder. Conventional cement powders moreover exhibit the phenomenon of the cement powder particles only being poorly wetted by methyl methacrylate owing to the different surface energies. The methyl methacrylate thus only penetrates relatively slowly into the cement powder.

Furthermore, with a vacuum effect, it cannot be ruled out that, after complete penetration of the cement powder by the monomer liquid, the monomer liquid is drawn off via the vacuum connection. There is then insufficient monomer liquid available for the hardening by radical polymerization or the mixing ratio is altered in an undesired manner, and therefore also the consistency of the bone cement paste. It is furthermore problematic that the air included between the cement powder particles is to be displaced from the top down by the monomer liquid since, owing to gravity, the air which is specifically lighter than the monomer liquid attempts to move upward in the cement powder and not to migrate downward in the direction of the vacuum connection.

Electrically driven pressing-out devices are also known from the field of adhesives and sealants. These devices can be driven both by accumulators and by batteries as well as with the aid of a stationary power supply. These devices can use their sometimes very high pressing-out forces to press out particularly tenacious paste-like masses. However, the use of electric motors can be disadvantageous in that they contain non-ferrous metals and are cost-intensive to purchase. In the operating area, which must be kept sterile, devices of this type have to undergo laborious sterilization or even be replaced. With electric cabling, the movement of the operator in the operating room can be obstructed.

Pneumatic devices have furthermore also been proposed. These devices require a stationary or mobile compressed-air connection (U.S. Pat. No. 2,446,501 A, DE 20 2005 010 206 U1). To this end, compressed-air hoses are required, which can obstruct the movement of the operator.

As an alternative to this, the use of compressed-gas cartridges for providing compressed gas is also possible. To this end, devices have been proposed in which the inflow of compressed gas is controlled by a valve and the flow of the viscous mass is additionally controlled by a second valve (US 2004/0074927 A1, U.S. Pat. No. 6,935,541 B1). In these devices, the gas cartridges are integrated in the devices. Systems of this type, which are connected to compressed gas or contain compressed-gas cartridges, always require a compressed-gas source, without which the systems are no longer operable.

In the unpublished DE 10 2016 121 607, a full-prepacked mixing system with a cartridge containing a bone cement powder was proposed. A delivery plunger is provided in the cartridge and a receptacle containing a monomer liquid container is arranged behind the cartridge. Located on the back side of the receptacle is a feed plunger by means of which the monomer liquid container can be pressed and the monomer liquid can be pressed out of the receptacle into the cartridge.

It has been illustrated in practical tests that the bone cement paste produced by this device always has a good consistency when a suitable cement powder is used. If the burst monomer liquid container is maximally compressed during the monomer transfer, then a good cement paste is reproducibly obtained. However, with certain configurations, an undesired change in the consistency of the bone cement paste at the end of the pressing-out procedure is possible, in which the mixing ratio between the cement powder and the monomer liquid has changed.

Within the context of the present embodiments, it has been found that this is linked to the selection and the stability of the monomer liquid container. With incomplete compression of the burst monomer liquid container, which can occur for example as a result of selecting a monomer liquid container with very stable walls, a residue of the monomer liquid can in fact remain within the fragments of the burst monomer liquid container between the delivery plunger and the feed plunger, which, at the end of the pressing-out of the bone cement paste, can escape through the delivery pipe as a result of a subsequent recompression of the burst monomer liquid container owing to an axial movement of the feed plunger in the direction of the delivery plunger.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
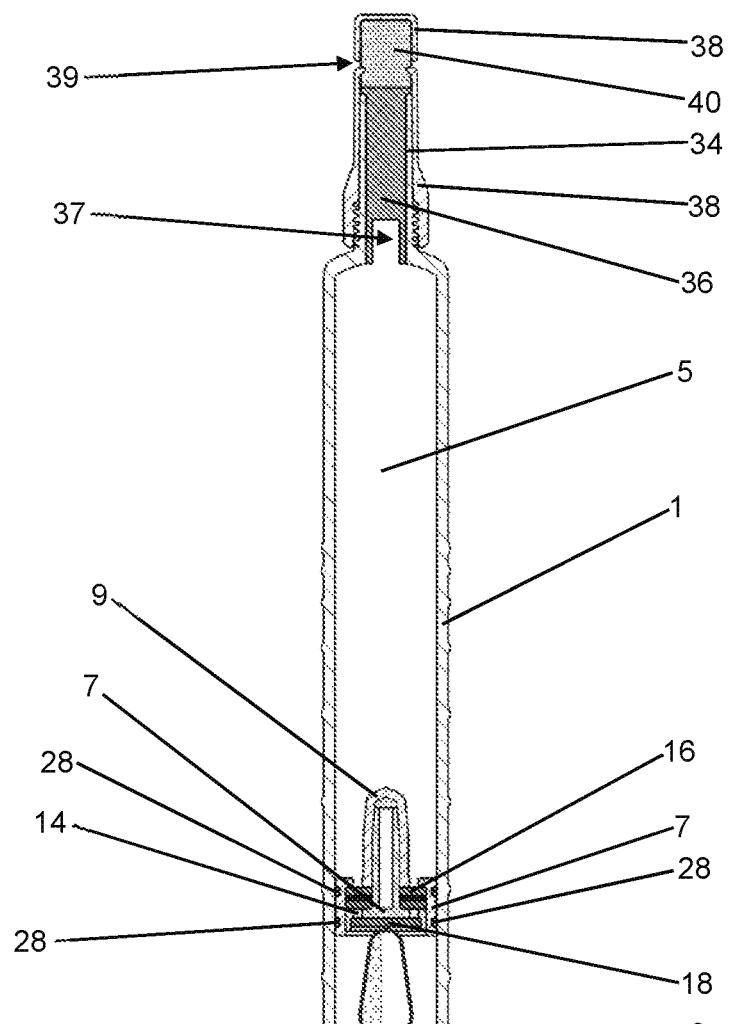
FIG. 1 illustrates a schematic cross-sectional view of an exemplary inventive device for storing and mixing a monomer liquid and a cement powder, which device is inserted into a pressing-out device.
Figure 1:
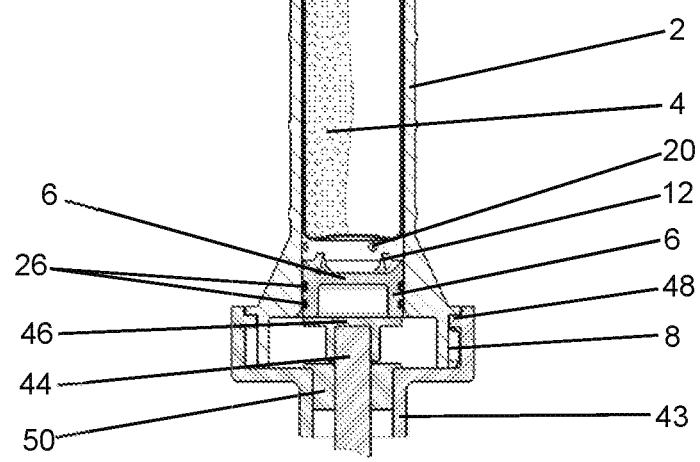

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

The object of the present embodiments are therefore to overcome the disadvantages of the prior art. One embodiment is a device which is provided and suitable for mixing the bone cement paste from the parent components and for delivering the mixed bone cement paste, and a method for producing a bone cement paste, in one embodiment, a paste-like polymethyl methacrylate bone cement paste, wherein the bone cement paste is produced from a cement powder and a monomer liquid by such a device with which the disadvantages of the previous devices and methods are overcome. One aspect is to improve such a device in such a way that, even in the event of an incomplete compression of the monomer liquid container at the end of the delivery of the bone cement paste, the monomer liquid is effectively prevented from escaping from the delivery pipe of the cartridge. By means of the device according to one embodiment and the method according to one embodiment, the intention is therefore to achieve that, even with a very simple and economical construction of the device and with a simultaneously very simple and uncomplicated operability of the device, a homogeneous bone cement paste can be generated and applied from the start to the end of the pressing-out procedure.

The device should be driven by a simple pressing-out device and, at the same time, be as simple as possible to operate. The construction should be economical so that the device can be used only once for reasons of hygiene. All, or as many as possible, of the processes executed in the device, such as the mixing of the parent components, the delivery of the bone cement paste and possibly also the opening of the monomer liquid container and possibly also the opening of the cartridge, should be executed with as few operating steps as possible and, as far as possible, in an automated manner, and should in one embodiment be driven by a single linear drive.

One embodiment, therefore, develops a device for mixing cement powder and monomer liquid. The handling of the device should be maximally simplified to essentially prevent application errors resulting from incorrectly implemented assembly steps. After removing the device from its packaging, the medical operator should connect it to a pressing-out device and then actuate this latter. The aim is to avoid further assembly and operating steps owing to the construction of the device. The device should in one embodiment also enable reliable storage of cement powder and monomer liquid in mutually separate compartments to rule out unintentional mixing of the cement components during the storage of the device. The device should enable sterilization with the gas ethylene oxide. The cement powder stored in the device has to be accessible to the ethylene oxide. The device should be activatable with the aid of a pressing-out device which is driven manually in the operating procedure so that, after the form- or force-fitting connection of the device to the pressing-out device, the axially drivable rod of the pressing-out device acts on the device as a result of actuating the pressing-out device, possibly opens the monomer liquid container and then transfers the monomer liquid into the cement powder upon a further movement of the rod. The mixing of the monomer liquid with the cement powder should take place without a mixer which needs to be moved manually from the outside. As far as possible, the mixing of the cement components to form the bone cement paste and the pressing-out of the mixed bone cement paste should be realized simply as a result of the forward movement of the rod of the pressing-out device. In one embodiment, as far as possible, the opening of the monomer liquid container and the subsequent monomer liquid transfer into the cement powder should be realized simply as a result of the forward movement of the rod of the pressing-out device.

So that the device as a whole is not substantially more complex, longer and larger than the mixing devices hitherto normally used for the conventional powder/liquid polymethyl methacrylate bone cements, the bone cement applicator to be developed should in one embodiment not require two rods which are connected to one another and are to be driven synchronously. The aim is to find a simple solution which, as far as possible, enables the bone cement paste to be expelled by means of a pressing-out device which includes only one rod and possibly a plate fastened thereto.

One embodiment is a device for producing a bone cement paste from a monomer liquid and a cement powder as parent components of the bone cement paste and for delivering the mixed bone cement paste, the device having a cartridge having a cylindrical interior, wherein the interior of the cartridge is closed on the front side except for a delivery opening for expelling the bone cement paste, wherein a delivery plunger, which is pushable in the direction of the delivery opening, is arranged in the interior of the cartridge and wherein the cement powder is arranged in the interior of the cartridge, between the delivery opening and the delivery plunger, wherein a closure means is arranged on the front side, facing the delivery opening, of the delivery plunger, which closure means closes the delivery opening when the delivery plunger is pressed against the front side of the interior of the cartridge, wherein the closure means and/or an additional spacer blocks a further movement of the delivery plunger in the direction of the front side of the cartridge so that the delivery plunger is spaced from the front side of the interior of the cartridge at least in some areas and a dead volume remains in the interior of the cartridge when the delivery plunger is pressed against the front side of the interior of the cartridge.

The device according to one embodiment also provided for storing the cement powder and in one embodiment also for storing the monomer liquid.

It can be provided that the delivery opening is arranged in the front side of the cartridge. A delivery pipe, which delimits the delivery opening, is in one embodiment arranged on the front side of the cartridge.

The spacer is arranged in the interior of the cartridge.

The fact that a dead volume remains in the interior of the cartridge means that a volume remains between the delivery opening, which is closed by the closure means, and the delivery plunger, which volume is filled with a mixture of the cement powder and the monomer liquid when the delivery plunger is pressed against the front side of the interior of the cartridge.

The fact that the delivery plunger is pressed against the front side of the interior does not mean, that the delivery plunger itself is in direct contact with the front side of the interior. Instead the closure means and/or the additional spacer is in direct contact with the front side of the interior, if the delivery plunger is pressed against the front side of the interior.

The cartridge is in one embodiment manufactured from a thermoplastics material, in one embodiment by means of an injection molding method.

The interior of the cartridge has a cylindrical geometry. The cylindrical shape is the simplest with which the interior of the cartridge can be realized. In terms of geometry, a cylindrical shape is understood to be the shape of a general cylinder with any base area, that is, not only a cylinder with a circular base area. The inside wall of the interior of the cartridge can therefore be realized by the cylinder lateral surface of a cylinder with any base area, in one embodiment with a different base area, that is, also with base areas which are not circular or not round. According to one embodiment, however, a cylindrical geometry with a rotationally symmetrical and one embodiment circular base area is preferred for the interior since this is the easiest to manufacture.

With one embodiment, it is also proposed that the closure means is a body projecting from the front side of the delivery plunger.

As a result, it is ensured that, by means of the closure means, a force can be exerted on the delivery opening which is useful for sealing the delivery opening. Moreover, the spacing of the delivery plunger from the front side of the interior of the cartridge can thus also be ensured.

The front side of the delivery plunger is in one embodiment planar except for the closure means.

According to a further development of one embodiment, it can be provided that the spacer is arranged on the front side of the delivery plunger, which faces the delivery opening of the interior of the cartridge, or on a cartridge head delimiting the front side of the interior of the cartridge.

If a spacer is required and the closure means itself is not used for spacing the delivery plunger from the front side of the interior of the cartridge, the construction of spacers in this position can be manufactured particularly simply and is economically realizable.

The interior of the cartridge is in one embodiment delimited on its front side by a cartridge head in which the delivery opening is arranged. It can likewise in one embodiment be provided that a delivery pipe, which extends the delivery opening, is arranged on the cartridge head.

It can furthermore be provided that the dead volume is at least 1 $cm^3$ in size, in one embodiment at least 3 $cm^3$ in size.

These dead volumes are sufficient to retain portions of the bone cement paste in the interior of the cartridge which have not been fully mixed and can be produced in the interior of the cartridge in the region of the delivery plunger. It can thus be prevented that poorly mixed bone cement paste or a bone cement paste with a changing composition, and therefore consistency, which is not usable, is delivered at the end of the delivery procedure.

It can furthermore be provided that the closure means forms a seal, in one embodiment when a pressure is exerted on the back side of the delivery plunger.

It is hereby achieved that not even small quantities of the poorly mixed bone cement paste present in the region of the delivery plunger are able to penetrate through the delivery opening.

It can in one embodiment also be provided that the closure means has an inclined, in one embodiment conical, sealing face which forms a seal against a circumferential sealing edge or sealing face of the delivery opening when the delivery plunger is pressed against the front side of the interior of the cartridge, or the delivery opening has an inclined, in one embodiment, conical, sealing face which forms a seal against a circumferential sealing edge or sealing face of the closure means when the delivery plunger is pressed against the front side of the interior of the cartridge.

Seals of this type are easy to realize and exhibit a high sealing effect under pressure on the back side. This is particularly the case when suitable materials are selected for the sealing faces and the sealing edges. The sealing edges should therefore in one embodiment have the same hardness as the sealing faces or have a greater hardness than the sealing faces.

To this end, the diameter of the base of the inclined or conical sealing face of the closure means has a larger diameter than the internal diameter of the delivery opening, or, to this end, the diameter of the base of the inclined or conical sealing face of the delivery opening has a larger diameter than the internal diameter of the sealing edge of the closure means. At the tip, the inclined or conical sealing faces have a smaller diameter than the corresponding sealing edges so that the closure means or a fitting projecting into the interior of the cartridge can be introduced in a simple manner at the delivery opening.

According to one embodiment of the device, it can be provided that the closure means is a pin which is slideable into the delivery opening, at least in some areas, in order to close the delivery opening.

It is hereby achieved that the sealing effect is increased as the delivery plunger is driven further or as the pressure on the back side of the delivery plunger increases further. This results in the delivery opening becoming better sealed as the pin is slid more deeply or more firmly into the delivery opening. Moreover, such a system which is closed in a leak-type manner via the pressure on the back side of the delivery plunger can be constructed simply and economically.

It can also be provided that at least one connection, which is permeable to the monomer liquid and gases but is impermeable to the cement powder, is provided in the delivery plunger, which connection connects the front side of the delivery plunger to the back side of the delivery plunger.

It is hereby prevented that the cement powder penetrates into the connection in the delivery plunger, reacts with the monomer liquid there and the connection is closed when the cement powder in the connection expands. At the same time, the monomer liquid can be introduced into the interior of the cartridge through the connection in the delivery plunger.

To this end, a filter which is permeable to the monomer liquid and to gases, in one embodiment, a porous filter, is arranged at the mouth of the at least one connection leading into the interior of the cartridge.

It can furthermore be provided that the at least one connection in the delivery plunger leads into the interior of the cartridge within the closure means, wherein the closure means is in one embodiment a projecting pin and the at least one connection leads into the interior of the cartridge through a plurality of radial bores in the lateral surface of the pin.

It is thus ensured that the monomer liquid flows into the interior of the cartridge in a central region, and therefore into the cement powder, and is thus less easily able to flow along the wall of the interior of the cartridge and past the cement powder in the direction of the delivery opening. A more thoroughly mixed bone cement paste is therefore achieved.

The connection can lead into the interior of the cartridge in the form of through-openings arranged concentrically around the closure means.

It can in one embodiment be provided that the device has a receptacle in which the monomer liquid, in one embodiment, a monomer liquid container containing the monomer liquid, is contained, wherein the back side of the cartridge is connected to the front side of the receptacle—in one embodiment connected in such a way that the interior of the cartridge is flush with the interior of the receptacle.

As a result, the device is also suitable for storing the monomer liquid and for mixing the monomer liquid with the cement powder within the device. The device is therefore a full-prepacked mixing system.

The receptacle is in one embodiment manufactured from a thermoplastics material, in one embodiment by means of an injection molding method.

As a result, the device can be manufactured economically as a hygienic single-use product.

In devices according one embodiment, in which the monomer liquid is arranged in a monomer liquid container within the device, it can be provided that the monomer liquid container is a glass ampoule, a plastic ampoule, a plastics film bag or an aluminum-plastics composite bag. The monomer liquid can be stored for a particularly long time in such monomer liquid containers.

It can in one embodiment also be provided that an interior of the receptacle and the interior of the cartridge are connected to one another via a connection which is permeable to the monomer liquid and to gases but impermeable to the cement powder.

It is hereby ensured that the cement powder does not penetrate into the interior of the receptacle through the connection, react prematurely with the monomer liquid there and then prevent the monomer transfer into the interior of the cartridge. The connection is in one embodiment arranged in the delivery plunger.

It can furthermore be provided that the receptacle has a cylindrical interior in which the monomer liquid, in one embodiment a monomer liquid container containing the monomer liquid, is arranged.

The interior of the receptacle has a cylindrical geometry. The cylindrical shape is the simplest with which the interior of the receptacle can be realized. In terms of geometry, a cylindrical shape is understood to be the shape of a general cylinder with any base area, that is, not only a cylinder with a circular base area. The inside wall of the interior of the receptacle can therefore be realized by the cylinder lateral surface of a cylinder with any base area, notably with a different base area, that is, also base areas which are not circular or not round. According to one embodiment, however, a cylindrical geometry with a rotationally symmetrical and in one embodiment circular base area is preferred for the interior since this is the easiest to manufacture.

It can furthermore be provided that a feed plunger is arranged in the receptacle, which feed plunger is movable in the longitudinal direction of the receptacle and is drivable from a back side of the receptacle in the direction of the front side, wherein the monomer liquid, in one embodiment a monomer liquid container containing the monomer liquid, is arranged between the feed plunger and the delivery plunger.

A full-prepacked mixing system is hereby provided, in which all parent components of the bone cement paste, namely the monomer liquid and the cement powder, are contained and can also be stored therein.

The feed plunger closes the receptacle in a liquid-tight manner on its back side.

In devices according to embodiments that have a feed plunger, it can alternatively or additionally be provided that the monomer liquid container inside the receptacle is to be opened, in one embodiment broken open or torn open, by a movement of the feed plunger in the direction of the front side of the receptacle.

As a result, it is achieved that the monomer liquid container can be opened by the axial linear movement of the feed plunger. A pressing-out device with only one rod as an axially linear drive can thus be used both to open the monomer liquid container and to press the monomer liquid into the cartridge and also to press the bone cement paste out of the cartridge.

It can furthermore in one embodiment also be provided that at least one ventilation opening is arranged in the wall of the receptacle, which ventilation opening connects the interior of the receptacle to the environment.

As a result, the interior of the receptacle can be sterilized with a sterilizing gas.

According to one embodiment, it can also be provided that the at least one ventilation opening is arranged closely in the region of the feed plunger in such a way that it is closed by a movement of the feed plunger in the direction of the front side of the receptacle before a monomer liquid container, which is arranged in the receptacle and in which the monomer liquid is contained, is opened by the movement of the feed plunger.

As a result, the monomer liquid cannot escape from the interior of the receptacle if the at least one ventilation opening is closed by the feed plunger moving in the direction of the front side of the receptacle before the monomer liquid container is opened by the movement of the feed plunger, that is, crushed, split or torn open by the feed plunger in the interior of the receptacle, for example.

It can in one embodiment be provided that the receptacle and the cartridge are formed in one piece by a tubular container.

This construction is the simplest and most economically realizable construction.

In one embodiment, it can also be notable in that the back side of the cartridge is connected to the front side of the receptacle in such a way that the interior of the cartridge is flush with the interior of the receptacle.

As a result, it can be ensured that firstly the feed plunger can be moved by a pressure exerted on the back side of the feed plunger and then the feed plunger can be used to drive the delivery plunger in that the feed plunger, together with the delivery plunger, is pushed further in the direction of the delivery opening.

It can furthermore be provided that a fastening means is arranged on the back side of the device for the purpose of fastening a pressing-out device with which the delivery plunger is pushable in the direction of the delivery opening. The device can thereby be connected and fastened to a pressing-out device with a drivable rod.

It can furthermore be provided that at least one protruding tip, edge and/or blade for breaking the monomer liquid container is arranged on the front side of the feed plunger.

By applying a defined force to a previously determined and spatially delimited point, the pressure on this point can be increased with the same force and a defined breaking of the monomer liquid container can therefore be achieved. The sequence of the breaking open of the monomer liquid container is thus reproducible.

It can be provided that the cement powder is in contact, in particular in full contact, with the front side of the delivery plunger, wherein the cement powder is in one embodiment pressed into the interior of the cartridge.

As a result, it is prevented that relatively large gas inclusions remain in the cartridge, which gas inclusions could result in gas inclusions in the bone cement paste during the mixing of the monomer liquid with the cement powder. This cannot occur with a tightly packed cement powder since the monomer liquid wets the particles of the cement powder effectively and the surface tension of the monomer liquid does not then allow any gas inclusions, or at least any relevant gas inclusions, between the particles of the cement powder.

It can in one embodiment also be provided that the delivery opening is closed on its front side by a closure, in particular by a plug, wherein the bone cement paste is pressable out of the cartridge through the delivery opening when the delivery opening is open, and wherein the closure is in one embodiment permeable to gases and impermeable to the cement powder.

The cartridge can thus be used effectively for storing the cement powder. The closure can be opened. The interior of the cartridge and the cement powder can be sterilized through the closure by evacuating and rinsing the interior of the cartridge with a sterilizing gas, such as ethylene oxide, when this closure is permeable to gases and impermeable to the cement powder.

The closure is in one embodiment a filter, in one embodiment a porous filter, which is permeable to gases and impermeable to the cement powder.

In this case, it can be provided that the closure has an indentation on the back side facing the interior of the cartridge, in which indentation the foremost part of the cement powder is contained.

It is thus achieved that the foremost part of the bone cement paste, which is contained in the indentation, can be removed with the closure. The monomer liquid reaches this part last when it is pressed into the cement powder from the back side. Therefore, a part of the bone cement paste which is less thoroughly mixed can thus be removed with the closure.

With the delivery plunger, the closure in one embodiment forms a closure system of the cartridge, which is to be opened by axial pressure exerted on the delivery plunger in the direction of the delivery opening.

It can furthermore be provided that a delivery pipe is arranged on the front side of the cartridge, wherein the bone cement paste is pressable out through the delivery pipe.

The device can thereby be used effectively for applying bone cement paste to points which are less easily accessible.

It can also be provided that the volume of the clearances between the cement particles of the cement powder in the interior of the cartridge is in the range of 22 volume percent to 40 volume percent relative to the total volume of the cement powder. The total volume of the cement powder in one embodiment corresponds to the volume of the interior of the cartridge which is delimited by the delivery plunger and by a closure in a delivery opening on the front side of the cartridge.

It can furthermore be provided that the cross-section of the interior of the cartridge is a maximum of 16 $cm^2$, in one embodiment a maximum of 5 $cm^2$.

It can analogously also be provided that the internal diameter of the cartridge is smaller than 50 mm, in one embodiment smaller than 20 mm.

Due to the small internal diameter, the cross-section of the interior of the cartridge is so small that the tenacious bone cement paste can be pressed out of the cartridge with the aid of a manually driven pressing-out device even when further flow-hindering lines, such as a hose, an application tube or a static mixer, are provided in the flow direction of the bone cement paste.

According to a further development, it can be provided that the volume of the monomer liquid in the device, in one embodiment the monomer liquid in a monomer liquid container in the device, is at least as high as the volume of the air-filled clearances between the cement powder particles in the cartridge, in one embodiment at least as high as the volume of the liquid lines between the interior of the cartridge and the interior of a receptacle in which the monomer liquid is contained plus the volume of the air-filled clearances between the cement powder particles in the cartridge.

As a result, it can be ensured that all of the cement powder can be wetted by the monomer liquid and a homogeneous bone cement paste is thus generated.

The objects on which the present embodiments are based are also achieved by a method for producing a bone cement paste, in one embodiment a paste-like polymethyl methacrylate bone cement paste, wherein the bone cement paste is produced from a cement powder and a monomer liquid by a device according to one embodiment by means of the following sequential steps:

a) inserting the device into a pressing-out device, the pressing-out device having an axially drivable rod, and pushing the monomer liquid into the interior of the cartridge so that the monomer liquid mixes with the cement powder, b) the delivery plunger is driven by the rod in the direction of the delivery opening of the cartridge, wherein, as a result of the movement of the delivery plunger, the mixture of the cement powder and the monomer liquid from the cartridge is expelled from the device as bone cement paste, and c) the delivery plunger meets the front side of the cartridge, wherein the closure means closes the delivery opening, a further movement of the delivery plunger in the direction of the delivery opening is blocked and a residual quantity of the mixture remains in the dead volume in the interior of the cartridge.

In this case, it can be provided that, in step a), the monomer liquid is pressed into the cartridge through at least one connection in the delivery plunger, which is impermeable to the cement powder but permeable to gases and the monomer liquid, in one embodiment pressed into the cartridge by a movement of a feed plunger which is driven by the rod of the pressing-out device.

It is hereby achieved that the flow direction of the monomer liquid has the same direction as the movement of the delivery plunger with which the bone cement paste is expelled from the cartridge. This has the advantage in one embodiment that a single unidirectional drive can be used both for pressing in the monomer liquid and for pushing out the bone cement paste. Conventional pressing-out devices such as manually driven cartridge guns are thus usable for the method according to one embodiment.

It can furthermore be provided that, in step a), firstly the insertion of the device into the pressing-out device takes place, after which a feed plunger, which is mounted inside a receptacle arranged on the back side of the cartridge such that it is movable in the receptacle, is driven by the rod in the direction of the cartridge, wherein, as a result of the movement of the feed plunger, a monomer liquid container in which the monomer liquid is contained is opened and the monomer liquid is pressed out of the receptacle into the cartridge, wherein the cement powder mixes with the monomer liquid in the interior of the cartridge.

As a result, the method is also suitable for the prior storage of the parent components. The method can thus be implemented at any time through the implementation of a compact full-prepacked system.

In this case, it can be provided that, during the driving of the feed plunger, the broken or slit-open or burst monomer liquid container is collapsed and at the same time gas is pushed out of the receptacle through a connection into the cartridge and is pushed outward by the cement powder in the cartridge.

It can furthermore be provided that, in step b), due to the pressure exerted on the mixture of the cement powder with the monomer liquid, a closure, in one embodiment a porous filter, is moved or pushed forward in a delivery opening on the front side of the cartridge, whereupon the closure is in one embodiment removed from the delivery opening and an application tube is then in one embodiment fastened to the front side of the cartridge.

It can thus be prevented that the cement powder contained in the cartridge can trickle out of the cartridge or the powder becomes contaminated from the outside. At the same time, the contents of the cartridge can be sterilized with a sterilizing gas such as ethylene oxide.

It can finally be provided that, in step c), the delivery opening is sealed by the closure means owing to the pressure exerted on the back side of the delivery plunger by the rod of the pressing-out device.

As a result, it is achieved that the opening of the device can take place by means of the same unidirectional drive with which the bone cement paste is also expelled from the cartridge. Only one linear drive is then necessary.

One aspect is based on the surprising realization that, by closing the delivery opening and retaining a small residue of the mixture of the cement powder and the monomer liquid produced in the cartridge in the interior of the cartridge, it is achieved that bone cement paste which has a changed consistency at the end of the pressing-out procedure is not delivered since the residual bone cement paste is retained in the cartridge and the delivery opening is closed. The delivery opening is closed more firmly or sealed more tightly as the force with which the delivery plunger is driven further becomes greater. It can thereby be prevented that the last residue of the bone cement paste, which could have other physical properties owing to a possibly changed mixing ratio, can still be pressed out.

In one embodiment, the device has the substantial advantages that the two parent components of the bone cement paste are stored in the closed cementing system and that the mixing of the parent components takes place in the closed device. This means that the device does not have to be filled by the operator. This is then a full-prepacked cementing system. The medical operator does not have any contact with the individual parent components of the bone cements. Nuisance due to odor is thus only minimal. In one embodiment, an advantage of the device is also that the monomer liquid is pressed into the cement powder as a result of the simple forward movement of a rod of a manually driven pressing-out device. In doing so, the air present between the cement powder particles is displaced by the monomer liquid. A homogeneous bone cement paste is produced without requiring manual mixing by means of mixing rods with mixing vanes. This means that manual mixing, which is prone to error, is no longer required. The operation of the device is maximally simplified. It constitutes a ready-to-use system.

In one embodiment, the advantages of devices and methods are based essentially on the fact that the linear forward movement, known per se, of rods of manually operated pressing-out devices are used such that, due to the continuous effect of the force of the linear forward movement of the rod, a monomer liquid container is firstly opened, the monomer liquid container is then compressed, whereby the monomer liquid escapes from the monomer liquid container and is pressed into compacted cement powder, wherein the air present between the cement powder particles is displaced by the pressed-in monomer liquid and, after the wetting of the cement powder particles by the monomer liquid, a bone cement paste is produced. The prerequisite for this is the use of a cement powder which is formulated such that it is wetted very effectively by the monomer liquid and can absorb this due to a capillary effect.

The device can be used as a hygienic single-use product since it can be manufactured to a very large extent from plastics material and because all parts including the interiors and the cement powder are sterilizable with the aid of ethylene oxide.

The device according to one embodiment is characterized in that the delivery plunger has, on the end side facing the cartridge head, a pin, a cap or another closure means which has a conically shaped design at the end facing the cartridge head, wherein the diameter of the base of the cone has a larger diameter than the internal diameter of the tubular delivery opening or the delivery pipe. In this case, the pin, the cap or the closure means is in one embodiment arranged such that, upon an axial movement of the delivery plunger in the direction of the cartridge head, it dips at least partially into the delivery pipe or seals this delivery pipe and closes it in a liquid-impermeable manner.

One embodiment is based on the idea that, at the end of the pressing-out procedure of the bone cement paste, as a consequence of the axial movement of the delivery plunger in the direction of the cartridge head, the pin or the cap or the closure means in general of the delivery plunger dips into the delivery opening with its cone or is pushed onto a fitting on the delivery opening. Upon a further axial movement of the delivery plunger in the direction of the cartridge head, the cone is pressed with increasing strength into the tubular delivery opening or pressed with increasing strength onto the fitting. A movement of the delivery plunger in the direction of the cartridge head is thus prevented and, at the same time, the delivery opening is closed and sealed in a liquid-tight manner. Upon a possible recompression of the burst monomer liquid container, monomer liquid is thus unable to escape through the delivery opening. This means that, after the successful delivery of the main part of the bone cement paste, the cartridge closes upon the further forward movement of the rod of the pressing-out device itself.

An exemplary inventive device for storing, mixing and delivering polymethyl methacrylate bone cement can have for example:

a) a hollow cylindrical container having a connecting element arranged at the cartridge end for connection to a pressing-out device;
b) a cartridge head, which terminates the hollow cylindrical container on the front side, wherein a feed-through to the receptacle of the delivery pipe is arranged as a delivery opening in the cartridge head, and wherein at least one feed-through connects the outside of the cartridge head to the inside of the cartridge head in a gas-permeable manner,
c) a delivery pipe,
d) a closure which is axially movable in the cartridge head and is gas-permeable but impermeable to powder particles, wherein the closure has a feed-through which leads from the underside to the upper side and is connected to the delivery pipe in a liquid-permeable manner on the upper side,
e) a feed plunger which is axially movably arranged in the container and closes the cartridge base in a liquid-impermeable manner,
f) a delivery plunger, which is arranged in the container to be axially movable between the closure and the feed plunger, wherein the delivery plunger has at least one connection between the two end faces which is liquid-permeable and impermeable to powder particles,
g) at least one monomer liquid container, which is arranged in the container, between the delivery plunger and the feed plunger,
h) an interior (the interior of the cartridge), in which the cement powder is arranged, wherein the interior is delimited by the inside wall of the container, the closure and the delivery plunger.

The container in this case includes the cartridge as the front part of the container, in which the cement powder is arranged, and a receptacle as the rear part of the container, in which the monomer liquid container is arranged.

A method according to one embodiment can be implemented for example by the exemplary device for mixing the cement powder with the monomer liquid to form bone cement paste by means of the following steps:

a) the pressing-out device is connected to the connecting element of the container;
b) the rod of the pressing-out device is driven;
c) the feed plunger is displaced in the direction of the cartridge head;
d) the at least one monomer liquid container is compressed between the delivery plunger and the feed plunger;
e) the monomer liquid container is burst or torn;
f) the burst or torn monomer liquid container is collapsed and the air is pressed out from the interior of the receptacle and the monomer liquid is pressed out by the feed plunger through the at least one connection of the delivery plunger and into the cement powder in the interior of the cartridge;
g) the monomer liquid is dispersed in the cement powder while at the same time displacing the air from the clearances of the cement powder particles;
h) the cement powder particles are wetted with the monomer liquid;
i) the air escapes from the cement powder through the gas-permeable closure;
j) the cement powder particles expand with the monomer liquid and the radical polymerization of the monomer liquid is initiated by the reaction of the accelerator with the initiator;
k) the bone cement paste is formed from the cement powder and the monomer liquid;
l) the closure in the delivery opening is opened as a result of the axial application of pressure by the bone cement paste pressed axially in the direction of the cartridge head;
m) the bone cement paste is pressed out through the delivery opening due to the forward movement of the delivery plunger and the feed plunger; and
n) the delivery plunger is moved axially in the direction of the cartridge head until the pin dips into the delivery opening and closes this or the cap is pushed onto the delivery opening and closes this or the closure means seals and closes the delivery opening.

An exemplary variant of the method is characterized by the following steps after step k) of the method described above:

k1) the closure is pressed out of the delivery opening, and
k2) the closure falls out of the delivery opening or a delivery pipe.

Without restricting the invention, further exemplary embodiments will be explained below with reference to nine schematically illustrated figures.

Drawings of a device according to embodiments are illustrated in FIGS. 1 to 9. FIGS. 1 to 3 and 5 illustrate various schematic overall views of the exemplary device. FIGS. 4 and 6 to 9 illustrates schematic cross-sectional views as detailed views in the form of detail enlargements through different regions of the device.

The device according to one embodiment consists substantially of a tubular container of plastics material, which, as a front part (at the top in FIGS. 1 and 2, on the left in FIGS. 3, 4, 6 to 9 and on the top left in FIG. 5), forms a cartridge 1 with a cylindrical interior and which, as a rear part, forms a receptacle 2 for a glass ampoule 3 (or plastics ampoule 3) as a monomer liquid container. The back side of the device is illustrated at the bottom in FIGS. 1 and 2, on the right in the drawings of FIG. 3 and on the bottom right in FIG. 5 as well as in FIGS. 4 and 6 to 9. The tubular shape of the container can be seen particularly clearly in the cross-sectional view of FIGS. 1 to 3. Both the interior of the cartridge 1 and the interior of the receptacle 2 are cylindrical with a circular base area. In this case, the diameters of the interior of the cartridge 1 and the diameter of the interior of the receptacle 2 are the same size. The container with the receptacle 2 and the cartridge 1 is in one embodiment produced from plastics material using an injection molding technique. The receptacle 2 therefore has a cylindrical interior into which the glass ampoule 3 is pushed. The monomer liquid 4 is located in the glass ampoule 3. A cement powder 5 is poured or in one embodiment pressed into the interior of the cartridge 1. The monomer liquid 4 and the cement powder 5 form the parent components for a PMMA bone cement, which can be produced by the device.

Owing to the glass ampoule 3, the monomer liquid 4 can be stored for a very long time in the receptacle 2 and thus in the device. The cement powder 5 can likewise be stored in the device for relatively long time periods. The device is thereby suitable for storing the monomer liquid 4 and the cement powder 5 as parent components of a bone cement paste of the PMMA bone cement. However, the device is also suitable and provided for mixing the bone cement paste from the parent components and for delivering the mixed bone cement paste.

Arranged in the receptacle 2 is a feed plunger 6 of plastics material, which is movable in the longitudinal direction in the cylindrical interior of the receptacle 2. The feed plunger 6 is arranged in the region of the back side of the receptacle 2. The glass ampoule 3 can be compressed in the receptacle 2 by the feed plunger 6 and split thereby in that the feed plunger 6 is pushed in the direction of the front side, that is, in the direction of the cartridge 1. The feed plunger 6 has, on the front side, wipers with which splinters of the glass ampoule 3 can be wiped off the inside wall of the receptacle 2. To this end, the wipers are in lateral contact with the inside wall of the interior of the receptacle.

Figure 2:
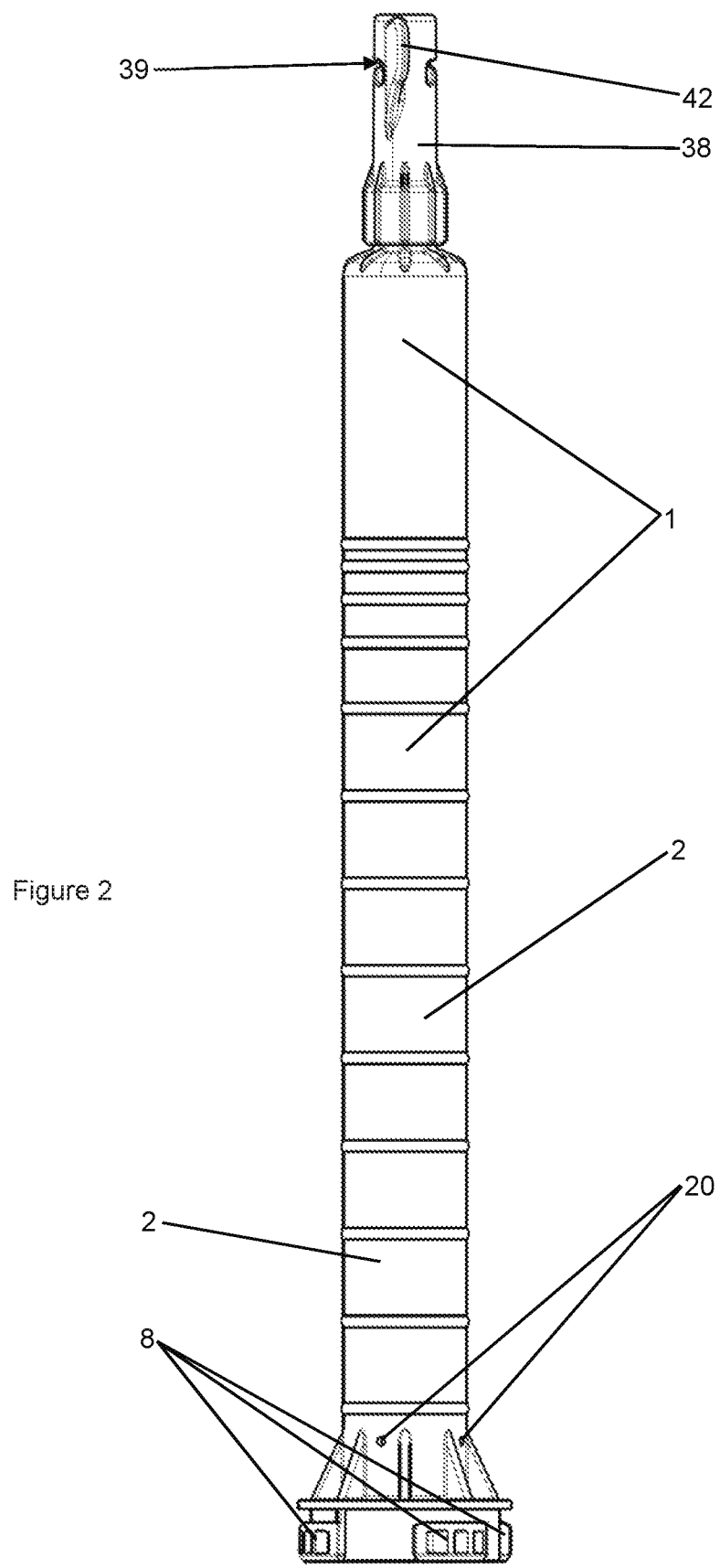
FIG. 2 illustrates a schematic side view of the device according to FIG. 1, which is not inserted into the pressing-out device.

A delivery plunger 7 of plastics material is arranged in the interior of the cartridge 1 in its back side (at the bottom in FIGS. 1 and 2 and on the right in FIGS. 3 and 4 to 9). Provided on the back side of the receptacle 2 is a fastening means 8 with which the receptacle 2 can be connected to a pressing-out device 43 (not illustrated in FIG. 2, but see FIGS. 1, 3, and 6). The fastening means 8 is in one embodiment suitable and provided for forming a bayonet closure 8. The feed plunger 6, which is freely accessible from the back side of the receptacle 2, can thus be driven in the direction of the front side of the cartridge 1 by the pressing-out device 43.

The delivery plunger 7 has, on its front side, a pin 9 as a closure means for closing a delivery opening on the front side of the interior of the cartridge 1. The pin 9 is rotationally symmetrical and has a steep and a flat conical region. The steep conical region of the pin 9 is used for sealing the delivery opening on the front side of the cartridge 1.

Wedges 12, which are provided for splitting or breaking the glass ampoule 3 when the feed plunger 6 is driven, are provided on the front side of the feed plunger 6.

The cartridge 1 and the receptacle 2 are constructed in one piece as a common plastics part. The receptacle 2 and the cartridge 1 are connected to one another via a connection 14 in the delivery plunger 7 such that they are liquid-permeable to the monomer liquid 4. The connection 14 through the delivery plunger 7 leads through a porous filter 16 into the interior of the cartridge 1, which porous filter is impermeable to the cement powder 5 but permeable to the monomer liquid 4.

In the mouth leading into the connection 14, a filter 18, by means of which the splinters of the glass ampoule 3 can be retained, is arranged in the delivery plunger 7. A screen can also be provided instead of the filter 18 or in addition to the filter 18.

A plurality of ventilation openings 20 are provided in the wall of the receptacle 2, through which ventilation openings the interior of the receptacle 2 can be sterilized with the aid of a sterilizing gas such as ethylene oxide. The ventilation openings 20 are arranged directly adjacent to the feed plunger 6 so that the feed plunger slides directly in front of the ventilation openings 20 and therefore closes the ventilation openings 20 directly when the feed plunger 6 is driven in the direction of the cartridge 1. It is thus prevented that monomer liquid 4 can escape through the ventilation openings 20 when the glass ampoule 3 in the receptacle has been opened.

The cylindrical feed plunger 6 has an outer circumference consistent with the cylindrical geometry of the interior of the receptacle 2 and is sealed against the inside wall of the receptacle 2 in a liquid-tight manner via two circumferential seals 26. The delivery plunger 7 is likewise sealed against the inside wall of the cartridge 1 in a liquid-tight manner via two circumferential seals 28. These seals 26, 28 serve to prevent monomer liquid 4 or bone cement from escaping so as to prevent contamination of the environment (the operating room and the operator). To this end, the seals 26, 28 can consist of rubber.

The interior of the cartridge 1 leads, on the front side, into a delivery pipe 34, which delimits the delivery opening of the cartridge 1. The delivery pipe 34 has an external thread in its base. A porous filter 36 as a closure for the cartridge 1 is arranged in the interior of the delivery pipe 34. The porous filter 36 is impermeable to the cement powder 5, but permeable to gases. An indentation 37 is provided in the back side of the porous filter 36. The cement powder 5 is also contained in the indentation 37. A cap 38 is fastened to the external thread of the delivery pipe 34, wherein the front part of the cap 38 is filled with an expanded polystyrene or foam material 40. Two wings 42 are provided on the cap 38 so that the cap 38 can be comfortably unscrewed from the delivery pipe 34 in the manner of a wing screw. The cap 38 has lateral openings 39. Owing to this construction, the interior of the cartridge 1 and the cement powder 5 can be sterilized with the aid of ethylene oxide since the openings 39 in the cap 38, the expanded polystyrene or the foam material 40, the porous filter 36 and the clearances between the powder particles of the cement powder 5 are air-permeable. At the same time, air can be pressed out of the receptacle 2 through the cement powder 5, the porous filter 36, the expanded polystyrene or the foam material 40 and the openings 39 in the cap 38 when the feed plunger 6 is pressed in the direction of the receptacle 2. Together with the expanded polystyrene or foam material 40 and with the porous filter 36, the cap 38 forms a closure for the delivery opening of the cartridge 1 or for the delivery pipe 34.

The cement powder 5 is enclosed in the cartridge 1 since all openings 39 and connections 14 are closed with the aid of the porous filter 16, 36 such that they are impermeable to the cement powder 5. In this case, the contents of the cartridge 1 can be sterilized by evacuation and rinsing with ethylene oxide. The device is thus also suitable for long-term storage of the cement powder 5.

Figure 3:
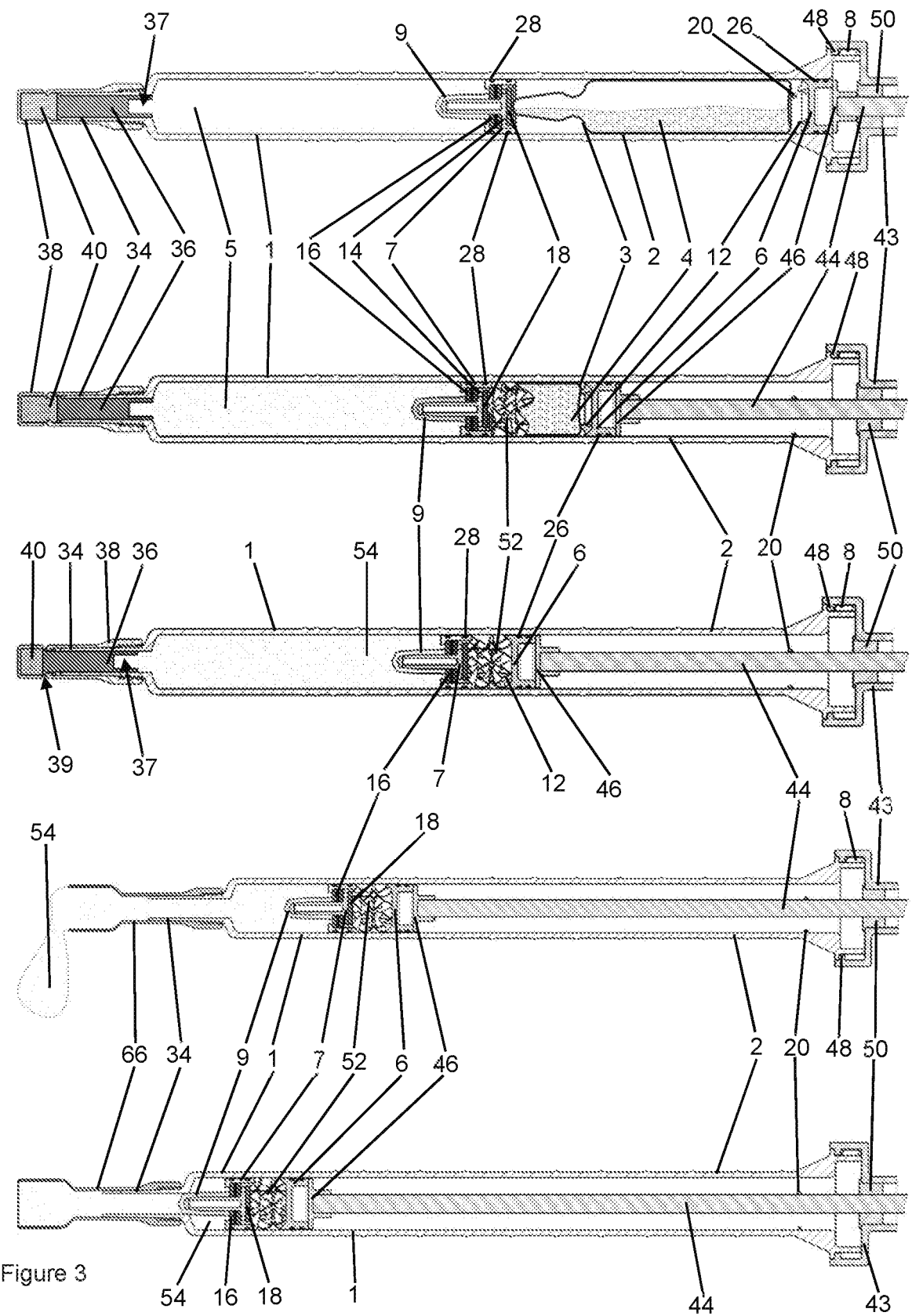
FIG. 3 illustrates the device according to FIGS. 1 and 2, with a connected pressing-out device, in five schematic cross-sectional views illustrated above one another to illustrate the sequence of a method according to one embodiment.
Figure 4:
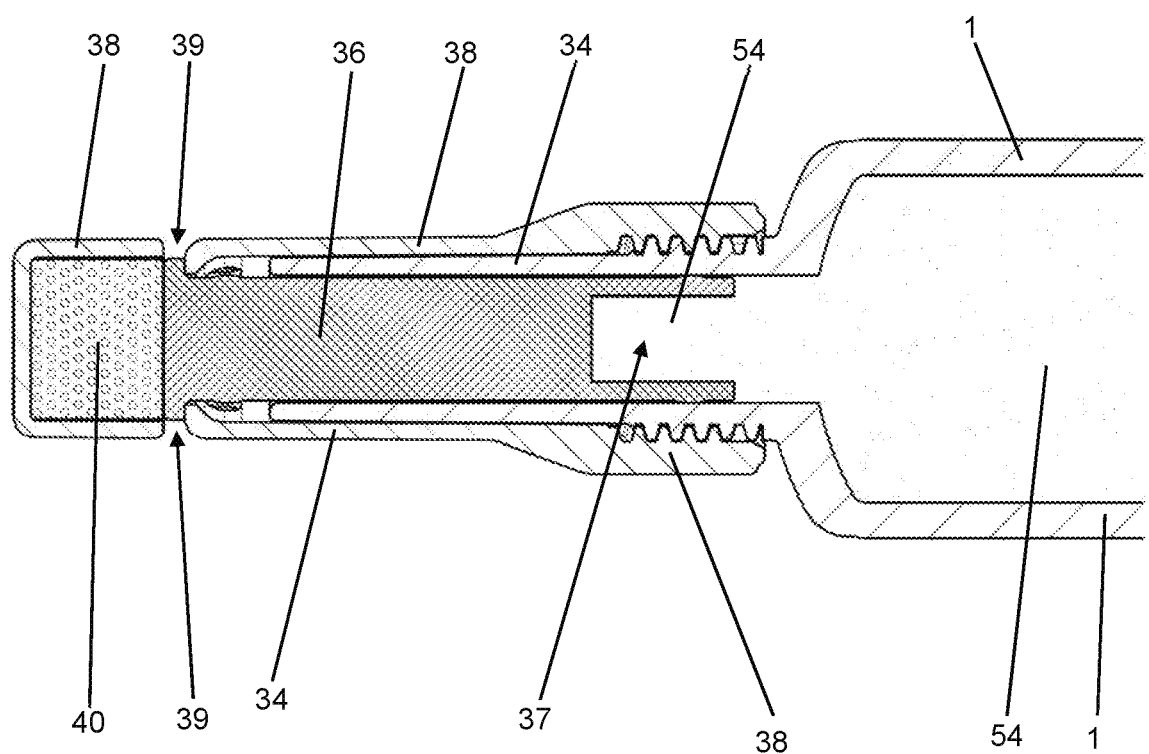
FIG. 4 illustrates a schematic cross-sectional view as a detail enlargement through the front part of the inventive device according to FIGS. 1 to 3 with the porous filter pushed forward.
Figure 6:
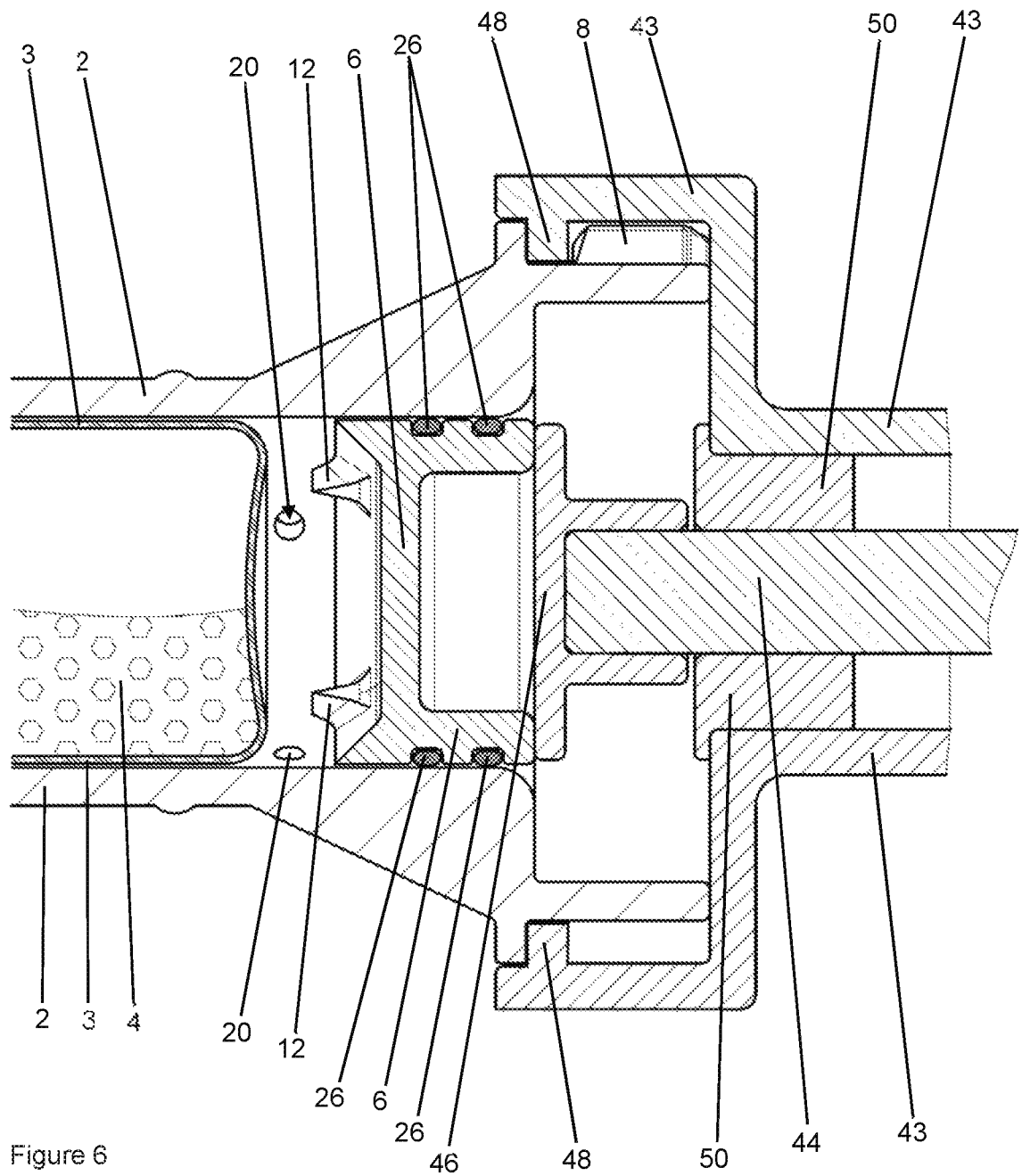
FIG. 6 illustrates a schematic cross-sectional view as a detail enlargement of the device in the starting state according to the first drawing from the top in FIG. 3, wherein the device is inserted into the pressing-out device.
Figure 7:
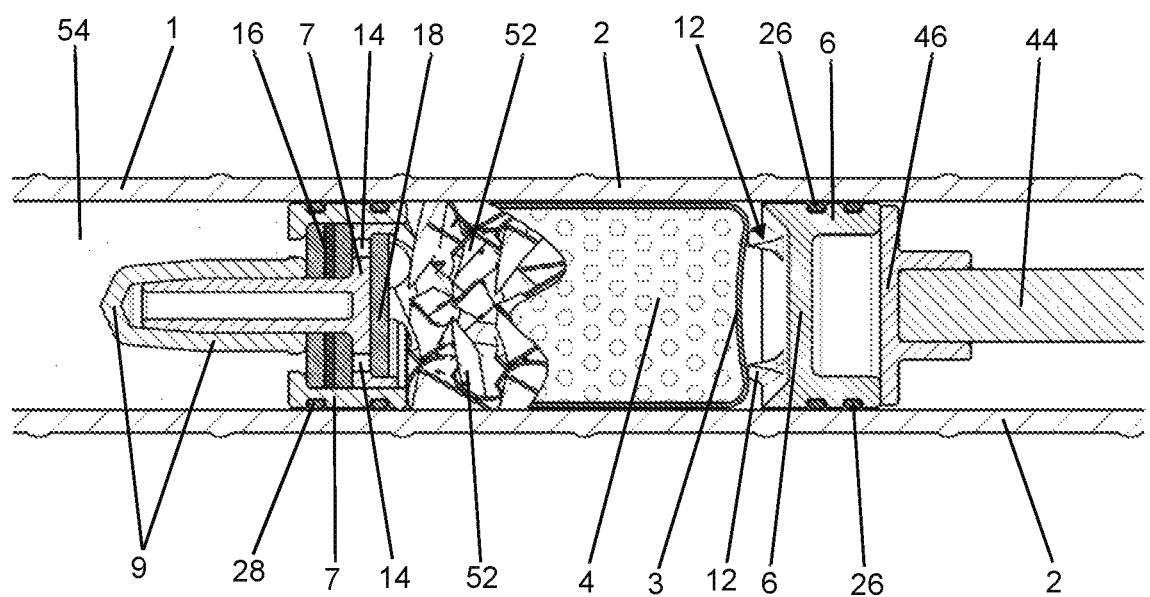
FIG. 7 illustrates a schematic cross-sectional view as a detail enlargement of the device according to the second drawing from the top in FIG. 3 during the pressing-in of the monomer liquid.
Figure 8:
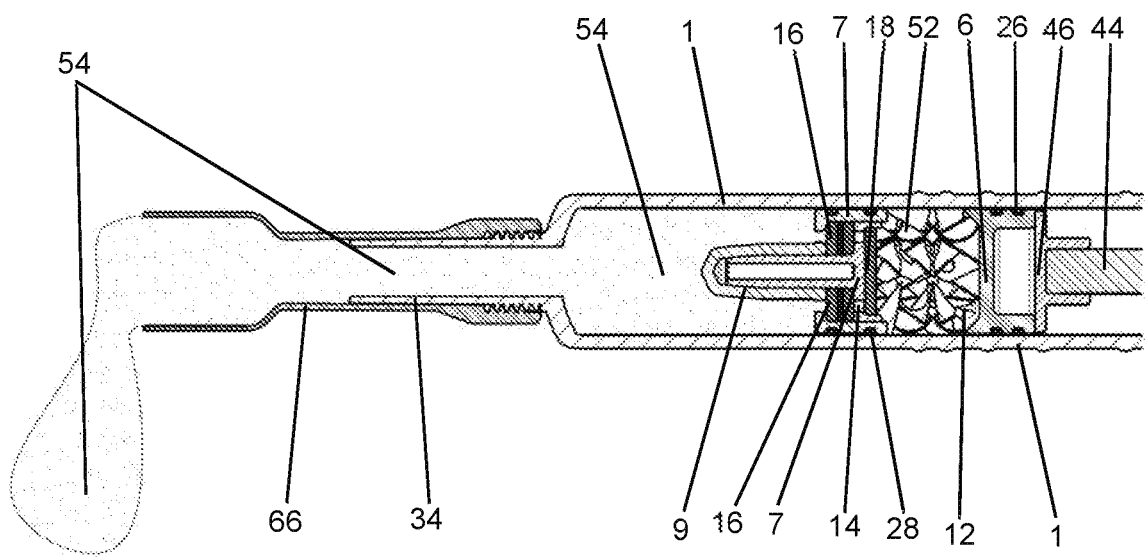
FIG. 8 illustrates a schematic cross-sectional view as a detail enlargement of the device according to the fourth drawing from the top in FIG. 3 during the delivery of the bone cement paste.
Figure 9:
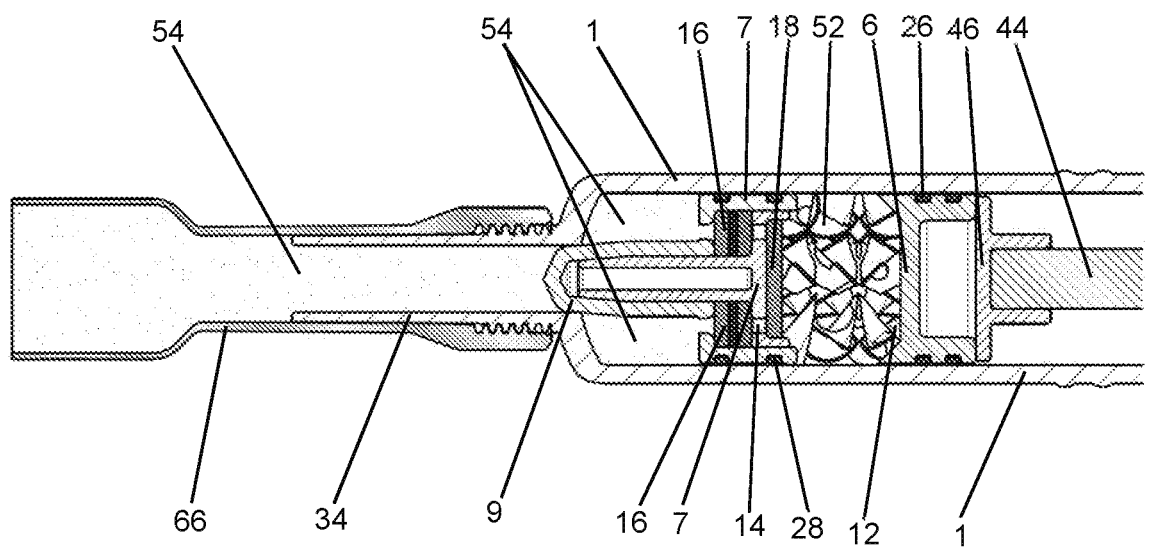
FIG. 9 illustrates a schematic cross-sectional view as a detail enlargement of the device according to the last drawing from the top in FIG. 3 with a closed delivery pipe or closed delivery opening.

FIG. 3 illustrates the inventive device according to FIGS. 1 and 2 in five schematic cross-sectional views illustrated above one another to illustrate the sequence of a method according to one embodiment. In addition, FIG. 4 illustrates a detail enlargement of the third drawing of FIG. 3, FIG. 6 illustrates a detail enlargement of the first drawing from the top in FIG. 3, FIG. 7 illustrates a detail enlargement of the second drawing from the top in FIG. 3, FIG. 8 illustrates a detail enlargement of the fourth drawing from the top in FIG. 3 and FIG. 9 illustrates a detail enlargement of the bottom-most drawing of FIG. 3.

At the start of the method, the device is in the starting state, as is also illustrated in FIG. 1. In this state, the device is inserted into a pressing-out device 43 according to one embodiment, which corresponds substantially to a conventional cartridge gun. This situation is illustrated in FIG. 1 and in the top-most drawing of FIG. 3 and in FIG. 6. The pressing-out device 43 includes a linearly drivable rod 44.

Only the front part of the pressing-out device 43 is illustrated. The pressing-out device 43 also includes a handle and a tilt lever (not illustrated in the drawings) for manually driving the rod 44 of the pressing-out device 43, as is also the case in conventional manually driven pressing-out devices. The device is fastened to the pressing-out device 43 by the fastening means 8 (see top-most drawing in FIG. 3 and in the detail in FIG. 6). A flat plate 46 for driving the feed plunger 6 is provided at the tip of the rod 44. The rod 44 pushes with the plate 46 onto the feed plunger 6 when the rod 44 is pushed into the receptacle 2 by the pressing-out device 43. To this end, the pressing-out device 43 is connected to the back side of the receptacle 2 via a counter-fastening means 48 so that the plate 46 pushes onto the feed plunger 6 when the rod 44 is driven and drives this feed plunger in the direction of the cartridge 1. To this end, the rod 44 is mounted to be linearly movable with respect to a bearing 50 and moreover with respect to the counter-fastening means 48 and therefore with respect to the receptacle 2.

The pressing-out device 43 is operated and the rod 44, and, with the rod 44, the feed plunger 6, is thereby driven in the direction of the cartridge 1. Since the glass ampoule 3 is in contact with the delivery plunger 7 on the front side, the interior of the receptacle 2 becomes smaller and the glass ampoule 3 breaks. The monomer liquid 4 escapes from the glass ampoule 3 into the interior of the receptacle 2. The delivery plunger 2 cannot be pushed, or cannot be pushed far, from the glass ampoule 3 in the direction of the porous filter 36 when the cement powder 5 is dry, that is, has not been wetted by the monomer liquid 4, since the dry cement powder 5 is not free flowing and blocks a movement of the delivery plunger 7. This situation is illustrated in FIG. 3, second drawing from the top, and in the enlarged detail view in FIG. 7. Overlying air from the receptacle 2 is pushed out of the device through the filter 18, the connection 14, the porous filter 16, through the clearances between the particles of the cement powder 5, through the porous filter 36, through the foam material 40 and out of the openings 39 in the cap 38.

Finally, all that remains of the glass ampoule 3 are splinters 52, which are retained by the filter 18 and remain in the tubular container. The monomer liquid 4 is pressed into the cement powder 5 through the filter 18, the connection 14 and the porous filter 16 and begins to react with the cement powder 5 there so that the bone cement paste 54 is formed from the mixture 54. The quantity of the monomer liquid 4 is selected such that the cement powder 5 is wetted with the monomer liquid to the front-most tip of the cartridge 1, that is, to the indentation 37 in the porous filter 36. This situation is illustrated in FIG. 3, third drawing from the top. As soon as the mixture 54 is produced, the porous filter 36 is driven forwards by the pressure exerted on the mixture 54 owing to the pressure on the delivery plunger 7 and compresses the foam material 40. When the porous filter 36 now slips forward, it is visible to the operator from the outside through the opening 39 in the cap 38. This situation is illustrated in detail in FIG. 4. To this end, the porous filter 36 in one embodiment has a different color and/or brightness to the foam material 40. For example, the foam material 40 can be white and the porous filter 36 red.

Figure 5:
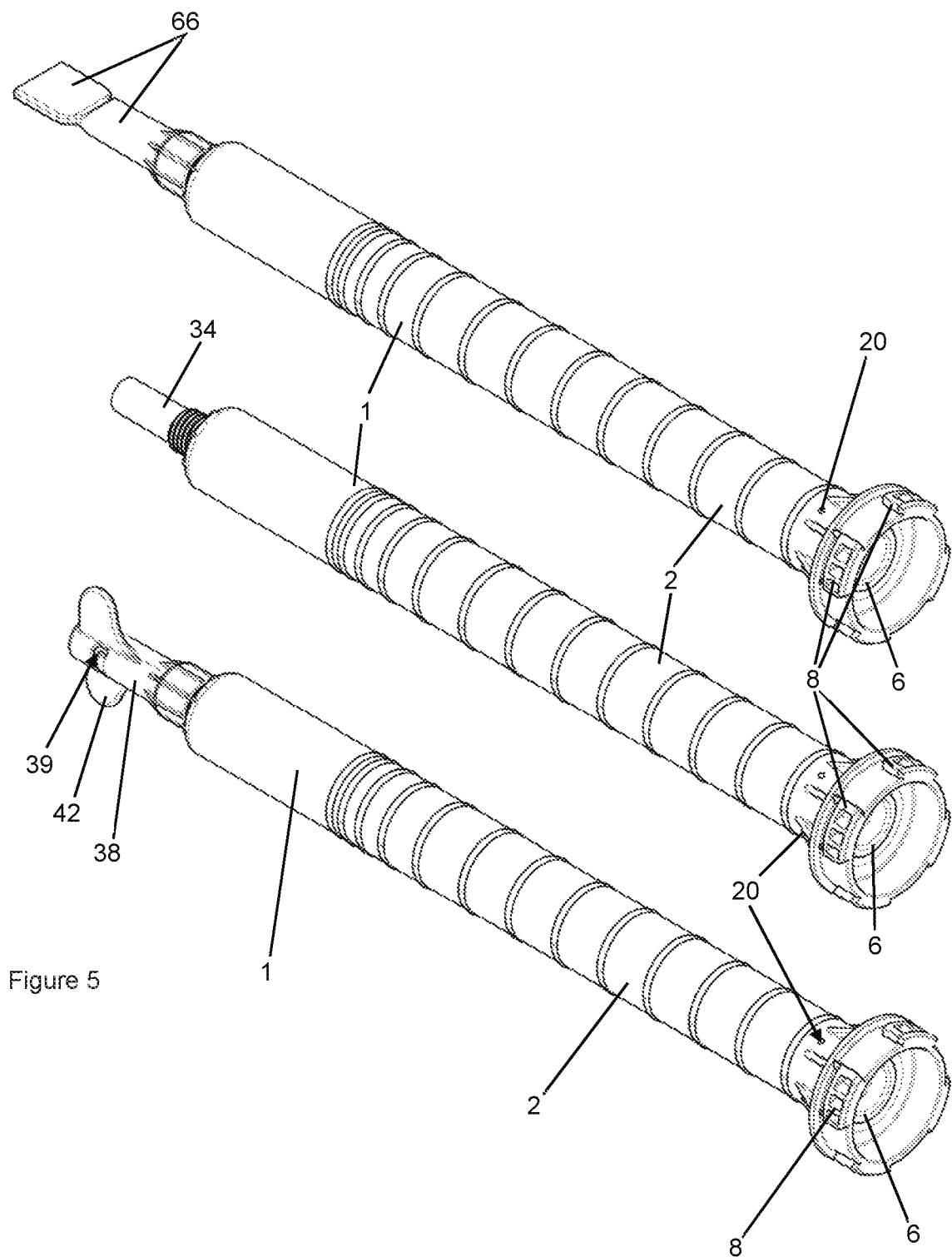
FIG. 5 illustrates three schematic perspective views of inventive devices according to FIGS. 1 to 4 with an application tube, without an attachment and with a cap on the delivery pipe.

In this state, the cap 38 with the porous filter 36 and the foam material 40 is unscrewed and, instead, an extended delivery opening in the form of an application tube 66 is screwed onto the delivery pipe 34 (see also FIG. 5). During the unscrewing of the cap 38, the front-most part of the mixture 54 or the bone cement paste 54, which is located in the indentation 37 of the porous filter 38, is removed with the cap 38 and the porous filter 36. A potentially poorly mixed part of the bone cement paste 54 is thus removed and greater homogeneity of the available bone cement paste 54 is therefore achieved.

As a result of driving the rod 44 further, the feed plunger 6, the shards 52 and the delivery plunger 7 arranged in front are driven. The bone cement paste 54 is then delivered out of the cartridge 1 via the application tube 66. To this end, the delivery plunger 7 is driven in the direction of the delivery pipe 34 by the rod 44 (see also the fourth drawing from the top in FIG. 3 and the detailed view according to FIG. 8 in this regard). The bone cement paste 54 from the interior of the cartridge 1 is expelled through the delivery pipe 34 and the application tube 66 and can be applied there or can theoretically be used for further processing.

Finally, the pin 9 meets the delivery opening of the cartridge 1. In this case, the conical pin 9 is firstly introduced into the delivery pipe 34. Since the base of the conical pin 9 has a larger external diameter than the internal diameter of the cylindrical delivery pipe 34 or the circular delivery opening, the conical region of the pin 9 will finish at the edge which forms the connection of the delivery opening to the interior of the cartridge 1. The circular edge of the delivery opening or the delivery pipe 34 is pushed into the conical lateral surface of the pin 9 in this case. This situation is illustrated in the bottom-most drawing of FIG. 3 and in FIG. 9 as a detail enlargement. The interior of the cartridge 1 closes more tightly as the delivery plunger 7 is pushed with greater strength forward.

Since the delivery plunger 7 is blocked at the end of the pressing-out procedure, the shards and splinters 52 of the glass ampule 3 can be further compressed by the increasing pressure exerted on the shards and splinters 52 and, with this, further residues of the monomer liquid 4 can be pushed out of the clearance between the delivery plunger 7 and the feed plunger 6 into the front part of the cartridge 1. This can cause a change in the composition of the bone cement paste 54 since the content of liquid monomer liquid 4 in the mixture 54 is increased. If the bone cement paste 54 has already reacted to a very large extent, it can also be that the monomer liquid 4 finds a way past the bone cement paste 54. Owing to the length of the pin 9, it is ensured that the front side of the delivery plunger 7 is spaced from the front side of the interior of the cartridge 1 when the delivery plunger 7 is pushed as far forward as a manually driven pressing-out device 43 allows. A dead volume is thus produced in the interior of the cartridge 1, which cannot be expelled from the cartridge 1 through the delivery opening and the delivery pipe 34.

The part of the bone cement paste 43 which possibly contains too high a content of monomer liquid 4 is now located in this dead volume. Even if the pressing procedure subsequently continues, this only further increases the sealing effect of the pin 9. As a result of this construction, it is ensured that bone cement paste 54 which has a different consistency owing to the changing composition cannot be applied with the device.

Alternatively to the pin 9 according to the exemplary embodiment illustrated, other closure means can also be used. For example, the delivery pipe 34 can project a short distance into the interior of the cartridge 1 and form a tubular fitting there. The closure means can then be realized by a cap with a conically tapering sealing face. Instead of the closure means, the delivery pipe or the delivery opening can furthermore naturally also have a conical face, which forms a seal with an edge or a likewise conical face of the closure means. Instead of conical faces, rounded surfaces can also be used for sealing. Therefore, for example, instead of the pin 9 with a conical face, a pin with an oval-shaped or ellipsoidal surface can also be used for sealing. In all of these embodiments of the closure means, it is important that a sealing effect is achieved. To this end, it is sufficient if full closure against the outer delimitation of the delivery opening is achieved. In this case, a further movement of the closure means into or onto the delivery opening should in one embodiment lead to a reinforcement of the sealing effect. Further embodiments of inventive closure means are therefore readily conceivable to the person skilled in the art on the basis of the explained principle.

The openings 39 also serve as visual markers, with the aid of which it can be established when the device is ready for use. If the porous filter 36 is pushed forward owing to the pressure of the bone cement paste 54 and, with this, the expanded polystyrene 40 is compressed in the cap 38, the porous filter 36 becomes visible through the openings 39. The operator can thus recognize that the bone cement paste 54 is present in the cartridge in its fully mixed state and is therefore ready for use. At this point in time, the operator can unscrew the cap 38 with the porous filter 36 and screw the application tube 66 onto the delivery pipe 34. The delivery plunger 7 can then be driven via the feed plunger 6 with the rod 44 and the bone cement paste 54 can thus be expelled from the cartridge 1 through the application tube 66.

The features of the invention which are disclosed in the description above as well as in the claims, figures and exemplary embodiments can be important to the realization of the in its various embodiments both individually and in any combinations.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A device for producing a bone cement paste from a monomer liquid and a cement powder as parent components of the bone cement paste and for delivering the mixed bone cement paste, the device comprising:
    a cartridge having a cylindrical interior, wherein the interior of the cartridge is closed on the front side except for a delivery opening for expelling the bone cement paste, wherein a delivery plunger, which is pushable in the direction of the delivery opening, is arranged in the interior of the cartridge and wherein the cement powder is arranged in the interior of the cartridge, between the delivery opening and the delivery plunger, the delivery plunger configured to expel the bone cement paste from the device when pushed toward the delivery opening;
    wherein a closure means is arranged on the front side, facing the delivery opening, of the delivery plunger, which closure means closes the delivery opening when the delivery plunger is pressed against the front side of the interior of the cartridge;
    wherein the closure means is a body projecting from and integrally fixed to the front side of the delivery plunger and seals the delivery opening when the delivery plunger is pressed against the front side of the interior of the cartridge; and
    wherein the closure means blocks a further movement of the delivery plunger in the direction of the front side of the cartridge so that the delivery plunger is spaced from the front side of the interior of the cartridge at least in some areas and a dead volume remains in the interior of the cartridge when the delivery plunger is pressed against the front side of the interior of the cartridge.

2. The device of claim 1, wherein the dead volume is at least 3 $cm^3$ in size.

3. The device of claim 1, wherein the closure means has an inclined sealing face which forms a seal against a circumferential sealing edge or sealing face of the delivery opening when the delivery plunger is pressed against the front side of the interior of the cartridge, or the delivery opening has an inclined sealing face which forms a seal against a circumferential sealing edge or sealing face of the closure means when the delivery plunger is pressed against the front side of the interior of the cartridge.

4. The device of claim 1, wherein the closure means is a pin which is slideable into the delivery opening, at least in part, in order to close the delivery opening.

5. The device of claim 1, wherein at least one connection, which is permeable to the monomer liquid and gases but impermeable to the cement powder, is provided in the delivery plunger, which at least one connection connects the front side of the delivery plunger to the back side of the delivery plunger.

6. The device of claim 5, wherein the at least one connection in the delivery plunger leads into the interior of the cartridge within the closure means.

7. The device of claim 1, wherein the device has a receptacle in which the monomer liquid or a monomer liquid container containing the monomer liquid is contained, wherein the back side of the cartridge is connected to the front side of the receptacle.

8. The device of claim 7, wherein an interior of the receptacle and the interior of the cartridge are connected to one another via a connection which is permeable to the monomer liquid and to gases but impermeable to the cement powder.

9. The device of claim 7, wherein the receptacle has a cylindrical interior in which the monomer liquid or the monomer liquid container containing the monomer liquid, is arranged.

10. The device of claim 7, wherein a feed plunger is arranged in the receptacle, the feed plunger being movable in the longitudinal direction of the receptacle and being drivable from a back side of the receptacle in the direction of the front side, wherein the monomer liquid or the monomer liquid container containing the monomer liquid, is arranged between the feed plunger and the delivery plunger.

11. The device of claim 10, wherein at least one protruding tip, edge or blade for breaking the monomer liquid container is arranged on the front side of the feed plunger.

12. The device of claim 7, wherein at least one ventilation opening is arranged in the wall of the receptacle, the ventilation opening connecting the interior of the receptacle to the environment.

13. The device of claim 12, wherein a feed plunger is arranged in the receptacle, the feed plunger being movable in the longitudinal direction of the receptacle and being drivable from a back side of the receptacle in the direction of the front side, wherein the monomer liquid or the monomer liquid container containing the monomer liquid is arranged between the feed plunger and the delivery plunger, and wherein the at least one ventilation opening is arranged closely in the region of the feed plunger in such a way that it is closed by a movement of the feed plunger in the direction of the front side of the receptacle before a monomer liquid container, which is arranged in the receptacle and in which the monomer liquid is contained, is opened by the movement of the feed plunger.

14. The device of claim 7, wherein the back side of the cartridge is connected to the front side of the receptacle in such a way that the interior of the cartridge is flush with the interior of the receptacle.

15. The device of claim 1, wherein a fastening means is arranged on the back side of the device for the purpose of fastening a pressing-out device with which the delivery plunger is pushable in the direction of the delivery opening.

16. The device of claim 1, wherein the delivery opening is closed on its front side by a by a closure, wherein the bone cement paste is pressable out of the cartridge through the delivery opening when the delivery opening is open.

17. The device of claim 1, wherein a delivery pipe is arranged on the front side of the cartridge, wherein the bone cement paste is pressable out through the delivery pipe.

18. The device of claim 1, wherein the cross-section of the interior of the cartridge is a maximum of 5 cm$^2$.

19. The device of claim 1, wherein the volume of the monomer liquid in the device is at least as high as the volume of the air-filled clearances between the cement powder particles in the cartridge.

20. A device for producing a bone cement paste from a monomer liquid and a cement powder as parent components of the bone cement paste and for delivering the mixed bone cement paste, the device comprising:
   a cartridge having a cylindrical interior, wherein the interior of the cartridge is closed on the front side except for a delivery opening for expelling the bone cement paste;
   wherein a delivery plunger, which is pushable in the direction of the delivery opening, is arranged in the interior of the cartridge and wherein the cement powder is arranged in the interior of the cartridge, between the delivery opening and the delivery plunger, the delivery plunger configured to expel the bone cement paste from the device when pushed toward the delivery opening;
   wherein a closure body is arranged on and integrally fixed to the front side, facing the delivery opening, of the delivery plunger, the closure body closing the delivery opening when the delivery plunger is pressed against the front side of the interior of the cartridge; and
   wherein the closure body blocks a further movement of the delivery plunger in the direction of the front side of the cartridge so that the delivery plunger is spaced from the front side of the interior of the cartridge at least in some areas and a dead volume remains in the interior of the cartridge when the delivery plunger is pressed against the front side of the interior of the cartridge.

21. A method for producing a bone cement paste, wherein the bone cement paste is produced from a cement powder and a monomer liquid by a device of claim 1, the method comprising the following sequential steps:
   a) inserting the device into a pressing-out device, the pressing-out device having an axially drivable rod, and pushing the monomer liquid into the interior of the cartridge such that the monomer liquid mixes with the cement powder;
   b) the delivery plunger is driven by the rod in the direction of the delivery opening of the cartridge, wherein, as a result of the movement of the delivery plunger, the mixture of the cement powder and the monomer liquid from the cartridge is expelled from the device as bone cement paste, and
   c) the delivery plunger meets the front side of the cartridge, wherein the closure body closes the delivery opening, a further movement of the delivery plunger in the direction of the delivery opening is blocked by the closure means which is a body projecting from the front side of the delivery plunger and a residual quantity of the mixture remains in the dead volume in the interior of the cartridge.

22. The method of claim 21, wherein in step a), the monomer liquid is pressed into the cartridge through at least one connection in the delivery plunger, which is impermeable to the cement powder but permeable to gases.

23. The method of claim 21, wherein in step a), firstly the insertion of the device into the pressing-out device takes place, after which a feed plunger, which is mounted inside a receptacle arranged on the back side of the cartridge such that it is movable inside the receptacle, is driven by the rod in the direction of the cartridge, wherein, as a result of the movement of the feed plunger, a monomer liquid container in which the monomer liquid is contained is opened and the monomer liquid is pressed out of the receptacle into the cartridge, wherein the cement powder mixes with the monomer liquid in the interior of the cartridge.

24. The method of claim 21, wherein in step b), due to the pressure exerted on the mixture of the cement powder with the monomer liquid, a closure is moved or pushed forward in a delivery opening on the front side of the cartridge.

25. The method of claim 21, wherein in step c), the delivery opening is sealed by the closure body owing to the pressure exerted on the back side of the delivery plunger by the rod of the pressing-out device.

26. The device of claim 1, wherein the dead volume is at least 1 cm$^3$ in size.

27. The device of claim 1, wherein the closure means has a conical sealing face which forms a seal against a circumferential sealing edge or sealing face of the delivery opening when the delivery plunger is pressed against the front side of the interior of the cartridge or the delivery opening has a conical sealing face which forms a seal against a circumferential sealing edge or sealing face of the closure means when the delivery plunger is pressed against the front side of the interior of the cartridge.

28. The device of claim 6, wherein the closure means is a projecting pin and the at least one connection leads into the interior of the cartridge through a plurality of radial bores in the lateral surface of the pin.

29. The device of claim 16, wherein the delivery opening is closed by a plug.

30. The device of claim 16, wherein the closure is permeable to gases and impermeable to the cement powder.

31. The device of claim 16, wherein the closure has an indentation on the back side facing the interior of the cartridge, in which indentation the foremost part of the cement powder is contained.

32. The device of claim 1, wherein the cross-section of the interior of the cartridge is a maximum of 16 cm$^2$.

33. The device of claim 1, wherein the volume of the monomer liquid in the device is at least as high as the volume of liquid lines between the interior of the cartridge and the interior of a receptacle in which the monomer liquid is contained plus the volume of the air-filled clearances between the cement powder particles in the cartridge.

34. The method of claim 21, wherein the bone cement paste is a paste-like polymethyl methacrylate bone cement paste.

35. The method of claim 22, wherein the monomer liquid is pressed into the cartridge by a movement of a feed plunger which is driven by the rod of the pressing-out device.

36. The method of claim 24, wherein by moving or pushing the closure forward in the delivery opening the closure is removed from the delivery opening.

37. The method of claim 36, wherein an application tube is then fastened to the front side of the cartridge.

38. The method of claim 24, wherein the closure is a porous filter.

* * * * *